United States Patent [19]

Engelbach et al.

[11] 4,151,182

[45] Apr. 24, 1979

[54] PRODUCTION OF ANTHRAQUINONE

[75] Inventors: Heinz Engelbach, Limburgerhof; Hermann Wistuba; Michael J. Sprague, both of Mannheim; Hans-Juergen Sturm; Herbert Armbrust, both of Gruenstadt, all of Fed. Rep. of Germany

[73] Assignee: Badische Anilin- & Soda-Fabrik Aktiengesellschaft, Fed. Rep. of Germany

[21] Appl. No.: 795,162

[22] Filed: May 9, 1977

Related U.S. Application Data

[63] Continuation of Ser. No. 689,170, May 24, 1976, abandoned, which is a continuation of Ser. No. 146,447, May 24, 1971.

[51] Int. Cl.$^2$ .................... C07C 45/00; C09B 1/00
[52] U.S. Cl. .................................... 260/369; 252/461
[58] Field of Search ................. 252/461; 260/369; 146/447; 689/170

[56] References Cited

U.S. PATENT DOCUMENTS

| 2,474,001 | 6/1949 | Levine | 252/461 X |
| 3,300,516 | 1/1967 | Vrbaski | 252/461 X |
| 3,306,915 | 2/1967 | Vrbaski | 252/461 |
| 3,658,893 | 4/1972 | Sturm et al. | 260/369 X |

OTHER PUBLICATIONS

Chem. Abs. 39137g, vol. 73, 1970, p. 269, Takeuchi et al.
J. Am. Chem. Soc., vol. 72, pp. 4918–4920, Spoerri et al.

Primary Examiner—Allen B. Curtis
Attorney, Agent, or Firm—Keil & Witherspoon

[57] ABSTRACT

The invention relates to a process for the production of anthraquinone by catalytic oxidation of indans or diphenylmethane derivatives with oxygen in the presence of a vanadium (V) compound with or without one or more than one compund of potassium, boron, thallium, antimony and/or caesium. Anthraquinone which can be prepared by the process according to this invention is a valuable starting material for the production of dyes and pesticides.

8 Claims, No Drawings

PRODUCTION OF ANTHRAQUINONE

This is a continuation of application Ser. No. 689,170 filed May 24, 1976, now abandoned.

U.S. patent application Ser. No. 49,166, now U.S. Pat. No. 3,699,134, filed June 23, 1970 discloses a process for the production of anthraquinone by catalytically oxidizing an indan having the general formula:

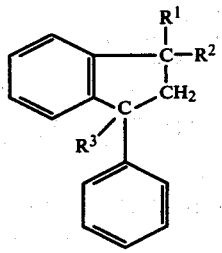

where $R^1$, $R^2$ and $R^3$ may be identical or different and each denotes an alkyl radical; $R^1$ and/or $R^2$ may also each denote a hydrogen atom; with oxygen in the gas phase.

We have now found that the process of the U.S. patent application Ser. No. 49,166, filed June 23, 1970 can be modified by carrying out the reaction with an indan having the formula (I) or with a diphenylmethane derivative having the general formula:

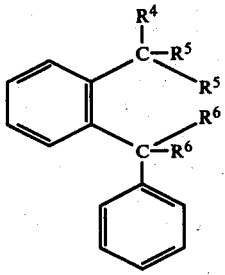

where $R^4$, $R^5$ and $R^6$ may be identical or different and each denotes a hydrogen atom or an aliphatic radical, or the pair of radicals $R^5$ and/or the pair of radicals $R^6$ may form an oxo group, and/or $R^4$ and one radical $R^6$ together may denote an aliphatic radical having a substituted methylene radical or having at least two carbon atoms, or both radicals $R^6$ or both radicals $R^5$ and both radicals $R^6$ may together denote an aliphatic radical as starting material in the presence of a vanadium (V) compound with or without one or more than one compound of potassium, boron, thallium, antimony and/or caesium.

Preferred starting materials (II) are those wherein in the general formula (II) the individual radicals $R^4$, $R^5$ and $R^6$ are identical or different and each denotes a hydrogen atom or an alkyl radical having one to eight, preferably 1 to 4, carbon atoms and if desired bearing a chlorine or bromine atom as a substituent, or the two radicals $R^5$ and/or the two radicals $R^6$ may in each case together denote an oxo group, and/or $R^4$ and one radical $R^6$ may together denote a methylene radical bearing as substituents chlorine atoms, bromine atoms or an alkyl group having one to three carbon atoms or may denote an alkylene radical having two to eight, preferably two to four carbon atoms which may bear chlorine atoms or bromine atoms as substituents.

In the preferred starting materials both radicals $R^5$ and one radical $R^6$ or one radical $R^5$ and both radicals $R^6$ may together denote an alkylidene radical having one to eight, preferably one to four, carbon atoms which may bear chlorine atoms or bromine atoms as substituents and which is attached to one of the adjacent carbon atoms by a double bond, or both radicals $R^5$ and both radicals $R^6$ together may also denote an alkylidene radical having two to eight, preferably two to four, carbon atoms which may bear chlorine atoms or bromine atoms as substituents and which is attached to two adjacent carbon atoms by a double bond in each case. The said radicals may be linear or branched. When both radicals $R^5$ are alkyl, $R^4$ particularly denotes hydrogen. When one radical $R^6$ is alkyl, the other radical $R^6$ preferably denotes hydrogen. The said radicals may bear as substituents groups and/or atoms which are inert under the reaction conditions, for example oxo, alkoxy, or alkyl having one to three carbon atoms.

The following are examples of compounds suitable as starting materials (II): 2-formylbenzophenone, 2-isopropylbenzophenone, 2-ethylbenzophenone and preferably 2-methylbenzophenone; 2-isopropyldiphenylmethane, 2-ethyldiphenylmethane, 2-formyldiphenylmethane and preferably 2-methyldiphenylmethane and corresponding homologs bearing methyl or propyl as a substituent on the methylene member; 2-chloro-1-oxo-3-phenylindan, 2-methoxy-1-oxo-3-phenylindan, 2-methoxyethyl-1-oxo-3-phenylindan, 2-ethyl-1-oxo-3-phenylindan and preferably the unsubstituted 1-oxo-3-phenylindan, 2-methyl-1-oxo-3-phenylindan or 2-bromo-1-oxo-3-phenylindan; 2-methyl-3-phenylindene, 3-methyl-3-phenylindene, 2-isopropyl-3-phenylindene and preferably 1-methyl-3-phenylindene; 2-ethyl-1-phenyltetrahydronaphthalene, 2,3-diethyl-1-phenyltetrahydronaphthalene, 4-methyl-1-phenyltetrahydronaphthalene, 4-propyl-1-phenyltetrahydronaphthalene, 2,3-dimethyl-1-phenyltetrahydronaphthalene, 2,4-dimethyl-1-phenyl-tetrahydronaphthalene, 3-methyl-4-ethyl-1-phenyltetrahydronaphthalene and preferably 1-phenyltetrahydronaphthalene; 1-phenylnaphthalene and its 2-chloro, 2,3-dimethyl and 4-ethyl derivatives; 1-phenylindene-(1) and its 3-methyl and 2-methyl compounds.

The starting materials (II) may be prepared by a conventional method, for example 2-benzyltoluene by reaction of benzyl chloride and toluene (Ber., 6, 906 (1873)), 1-oxo-3-phenylindan by reaction of trans-cinnamic acid and benzene (J. Amer. Chem. Soc., 65, 59 (1943)), 1-phenyltetrahydronaphthalene from styrene by thermal dimerization (J. Amer. Chem. Soc., 90, 1289 (1968)), 2-methylbenzophenone by reaction of benzene and o-toluyl chloride (Ber., 24, 2805 (1891)), 1-oxo-2-methyl-3-phenylindene by reaction of 2-methyl-3,3-diphenylacrylic acid (J. Amer. Chem. Soc., 67, 430 (1945)), 1-oxo-2-bromo-3-phenylindan by bromination of 1-oxo-3-phenylindan (Monatsh., 48, 342 (1927)), 2-methyl-1-phenylindene from β-methyl-γ-phenylcinnamyl alcohol (Ber., 55, 3414 (1922)). The homologs of the said starting materials may be obtained by analogous methods.

Otherwise, the process is carried out with the starting materials (II) in the presence of vanadic compounds and in the absence of the said additional compounds under the conditions of the process according to the U.S. patent application Ser. No. 49,166, filed June 23, 1970 particularly as regards reaction control, oxidation conditions, and production and composition of the catalyst.

When using vanadic compounds and also the said compounds of the additional elements as catalysts and the starting materials (I) or (II), the following reaction conditions are advantageous. In the case of 1-methyl-3-phenylindan the loading may be from 5 to 100, advantageously from 10 to 60, particularly from 25 to 50, grams of catalyst (or catalyst on carrier) per cubic meter (STP) of air. It is advantageous to use from 20 to 2000, more advantageously from 40 to 500, grams of starting material (I) or (II) per liter of catalyst (or catalyst on carrier) per hour, and one or more vanadic compounds and one or more compounds of potassium, boron, thallium, antimony and/or caesium may be present in the catalyst. Independently of the composition of the compound and the valency of the metal in the compound, the atomic ratio of vanadium in the catalyst to the additional element potassium, boron, thallium and/or antimony is advantageously from 1000 to 5 of vanadium to 1 of additional element. Atomic ratios of from 800 to 3, particularly 500 to 4 of vanadium to 1 of antimony, from 500 to 10, particularly 200 to 15 of vanadium to 1 of potassium, less than 800, particularly from 600 to 12, preferably from 500 to 20 of vanadium to 1 of thallium and from 100 to 1, particularly from 20 to 5 of vanadium to 1 of boron, are preferred. The atomic ratio of vanadium to additional element caesium is advantageously from 2000 to 5 of vanadium to 1 of caesium, preferably from 1000 to 12, particularly from 200 to 15 of vanadium to 1 of caesium. When antimony, potassium, thallium and/or boron are used as catalyst components as well as caesium, there are preferred (besides the atomic ratios specified for caesium) atomic ratios of 800 to 3, particularly 500 to 4 of vanadium to 1 of antimony, from 500 to 10, particularly from 200 to 15 of vanadium to 1 of potassium, less than 800, particularly from 600 to 12, advantageously from 500 to 20 of vanadium to 1 of thallium and from 100 to 1, preferably from 20 to 5 of vanadium to 1 of boron. The catalysts are advantageously used together with a carrier material, for example pumice, titanium dioxide, steatite, silicon carbide, iron oxide, silicon oxide, aluminium oxide or aluminum silicates such as mullite.

The compounds of the additional elements may be chosen at will; they are generally the oxides, acids, bases or salts, for example carbonates, bicarbonates, chlorides or nitrates, and those compounds of the additional elements which are converted to the oxides during the production of the catalyst or the reaction.

The following are examples of additional compounds: antimony trichloride, potassium carbonate, boron trioxide, thallium nitrate, boric acid, potassium hydroxide, antimony trioxide, antimony tetraoxide, antimony pentoxide, potassium nitrate, potassium bicarbonate, potassium oxalate, potassium formate, thallium acetate, thallium carbonate, ammonium borate, caesium oxide, caesium hydroxide, caesium carbonate, caesium nitrate, caesium bicarbonate, caesium oxalate, caesium formate, caesium acetate and caesium hydrogen tartrate.

The catalytically active components may be applied to the inert carriers by a conventional method (Houben-Weyl, "Methoden der organischen Chemie", volume 4/2, pages 143 to 240), for example by impregnation, spraying or precipitation, followed by calcination of the supported catalyst thus prepared.

Otherwise, the process is carried out under the conditions of the process according to the U.S. patent application Ser. No. 49,166, filed June 23, 1970, particularly as regards reaction control and the production and composition or the catalyst. It has proved to be advantageous to make catalysts containing vanadium pentoxide on spheroidal carriers by a flame spraying or plasma spraying method, for example according to the methods described in German Pat. No. (patent application P 20 25 430.2). The said additional compounds may be mixed mechanically with the vanadium pentoxide to be applied by means of flame spraying or with a compound, as for example vanadic acid, which is converted into vanadium pentoxide on heating. It may be advantageous however first to prepare a homogeneous solution which contains the elements to be applied. The compound to be applied may be recovered from this solution, for example by evaporation (see Example 1). The additional compounds chosen advantageously have a melting point below 1200° C. so as to ensure adequate adhesion to the carrier. Such compounds are particularly preferred in cases in which the additional element is present in large amounts. In the case of compounds having a higher melting point it may be necessary to use a plasma burner. In this case it is advantageous to avoid partial or complete reduction of vanadium(V) to vanadium(IV) so as to prevent the formation of the higher melting point vanadium(IV). Oxidation is advantageously carried out at a temperature of from 250° to 500° C., particularly from 300° to 450° C. This temperature is as a rule measured as the temperature of the coolant, for example a niter bath (tube wall temperature). A bleed stream of the reaction offgas which contains less oxygen may be saturated with the vapor of the starting material in order to set up the desired concentration of indan (I) in the reaction mixture.

In a preferred embodiment of the process according to the invention the catalyst or advantageously the catalyst applied to a carrier in any manner, preferably by the abovementioned flame spraying or plasma spraying method, is advantageously heated to a temperature of from 450° to 650° C., preferably from 500° to 600° C., and kept at this temperature for some time (calcination). The calcination period is advantageously from one hour to twenty-four hours, particularly from five to sixteen hours. Calcination is preferably carried out in the presence of gas containing oxygen, for example air or flue gas, and at a pressure of from 1 to 3 atmospheres. Reference is made to Ullmanns Encyklopadie der technischen Chemie, volume 9, pages 254 et seq for further details of the production of the catalysts.

The following Examples illustrate the invention. The parts given in the Examples are by weight. They bear the same relation to parts by volume as the kilogram to the liter.

EXAMPLES

Production of vanadium-antimony catalysts

EXAMPLE 1

100 parts of powdered vanadium pentoxide is homogeneously mixed with a solution of 1.57 parts of antimony trichloride in 0.5 part of concentrated hydrochloric acid, made neutral with concentrated ammonia solution and evaporated to dryness. Nitric acid is added and the whole is evaporated with fuming to expel the ammonia as ammonium nitrate, after which the mixture is fused and powdered. 10.0 parts of the powdered material is applied by means of flame spraying equipment to 90 parts of silicon carbide spheres having a diameter of from 4 to 6 mm.

EXAMPLE 2

The catalyst is prepared analogously to Example 1 but adding 7.85 parts of antimony trichloride to 100 parts of vanadium pentoxide.

EXAMPLE 3

The catalyst is prepared analogously to Example 1 but 15.7 parts of antimony trichloride is added to 100 parts of vanadium pentoxide.

EXAMPLE 4

48 parts of the catalyst prepared according to Example 1 is charged into a tubular reactor (inside diameter of the tubes: 21 mm). A mixture of 213,000 parts by volume of air and 7.68 parts of 1-methyl-3-phenylindan is passed per hour through the catalyst. The tube wall temperature is 395° C. and the temperature in the interior of the catalyst bed is 450° C. The gaseous reaction mixture leaving the reactor is cooled to 50° C. so that the end product and unreacted 1-methyl-3-phenylindan are condensed. The uncondensed portion is washed out with water. After the wash water has been evaporated, the residue which remains is combined with the condensate.

The following results are obtained:
Starting material: 1-methyl-3-phenylindan—23.05 parts
amount of offgas—636,000 parts by volume
content of CO and $CO_2$ in offgas—1.75% by volume
crude end product—20.54 parts.

The following are determined in the crude end product by ultraviolet absorption:
67.3% by weight of anthraquinone—13.8 parts
21% by weight of phthalic anhydride—4.3 parts
0.4% by weight of unreacted starting material (I)—0.08 part This is equivalent to a conversion of 99.6% of theory and a yield of anthraquinone of 60.2% of theory based on starting material reacted.

EXAMPLE 5

48 parts of the catalyst prepared according to Example 2 is placed in a tubular reactor (inside diameter of the tubes 21 mm). A mixture of 105,000 parts by volume of air and 3.78 parts of 1-methyl-3-phenylindan is passed per hour through the catalyst. The tube wall temperature is 370° C. and the temperature in the interior of the catalyst bed is 420° C. The gaseous reaction mixture leaving the reactor is cooled to 50° C. so that the end product and unreacted 1-methyl-3-phenylindan condense. The uncondensed portion is washed out with water. After the wash water has been evaporated, the residue which remains is united with the condensate.

The following results are obtained:
Starting material: 1-methyl-3-phenylindan—11.35 parts
amount of offgas—315,000 parts by volume
content of CO and $CO_2$ is offgas—1.70% by volume
crude end product—10.23 parts.

The following are determined in the crude end product by ultraviolet absorption:
67.2% by weight of anthraquinone—6.9 parts
20.4% by weight of phthalic anhydride—2.09 parts
0.1% by weight of unreacted starting material (I)—0.01 part This is equivalent to a conversion of 99.9% of theory and a yield of anthraquinone of 60.6% of theory based on reacted starting material.

EXAMPLE 6

48 parts of the catalyst prepared according to Example 3 is placed in a tubular reactor (inside diameter of the tubes 21 mm). A mixture of 100,000 parts by volume of air and 4.83 parts of 1-methyl-3-phenylindan is passed per hour through the catalyst. The tube wall temperature is 375° C. and the temperature in the interior of the bed of catalyst is 432° C. The gaseous reaction mixture leaving the reactor is cooled to 50° C. so that end product and unreacted 1-methyl-3-phenylindan are condensed. The uncondensed portion is washed out with water. After the wash water has been evaporated, the residue which remains is added to the condensate.

The following results are obtained:
Starting material: 1-methyl-3-phenylindan—14.49 parts
amount of offgas—300,000 parts by volume
CO and $CO_2$ content in offgas—1.95% by volume
crude end product—12.53 parts.

The following are determined in the end product by ultraviolet absorption:
74.3% by weight of anthraquinone—9.31 parts
15.6% by weight of phthalic anhydride—1.95 parts
0.1% by weight of unreacted starting material (I)—0.01 part This is equivalent to a conversion of 99.9% of theory and an anthraquinone yield of 64.3% of theory based on starting material reacted.

Production of vanadium-potassium catalysts

EXAMPLE 7

A mixture of 16.86 parts of vanadium pentoxide and 0.64 part of potassium carbonate (particle size less than 200 microns) is sprayed onto 152.1 parts of steatite spheres having a diameter of 3 mm by means of flame spraying equipment. The catalyst is then sintered at about 650° C.

EXAMPLE 8

The catalyst is prepared analogously to Example 7, a mixture of 14.48 parts of vanadium pentoxide and 0.023 part of potassium carbonate being sprayed onto 152.1 parts of steatite spheres.

EXAMPLE 9

The catalyst is prepared analogously to Example 7, a mixture of 11.06 parts of vanadium pentoxide and 0.088 parts of potassium carbonate being sprayed onto 152.1 parts of steatite spheres.

EXAMPLE 10

The catalyst is prepared analogously to Example 7, a mixture of 8.83 parts of vanadium pentoxide and 0.67 part of potassium carbonate being sprayed onto 152.1 parts of steatite spheres.

EXAMPLE 11

The catalyst is prepared analogously to Example 7, a mixture of 11.46 parts of vanadium pentoxide and 1.74 parts of potassium carbonate being sprayed onto 152.1 parts of steatite spheres.

Oxidation

EXAMPLE 12

80.0 parts of the catalyst prepared according to Example 7 is placed in a tubular reactor (inside diameter of the tubes 21 mm). A mixture of 100,000 parts by volume of air and 3.99 parts of 1-methyl-3-phenylindan is passed per hour through the catalyst. The tube wall temperature is 411° C. and the temperature in the interior of the bed of catalyst is 465° C. The gaseous reaction mixture leaving the reactor is cooled to 50° C. so that end product and unreacted 1-methyl-3-phenylindan are condensed. The uncondensed portion is washed out with water. After the wash water has been evaporated, the residue remaining is added to the condensate.

The following results are obtained:
Starting material: 1-methyl-3-phenylindan—19.95 parts
amount of offgas—500,000 parts by volume
CO and $CO_2$ content in offgas—2.0% by volume
crude end product—17.88 parts.

The following are determined in the crude end product by ultraviolet absorption:
67% by weight of anthraquinone—11.98 parts
19% by weight of phthalic anhydride—3.40 parts
0.15% by weight of unreacted starting material (I)—0.03 part.

This is equivalent to a conversion of 99.9% of theory and a yield of anthraquinone of 60.1% of theory.

EXAMPLE 13

76.0 parts of the catalyst prepared according to Example 8 is placed in a tubular reactor (inside diameter of the tubes 21 mm). A mixture of 100,000 parts by volume of air and 4.31 parts of 1-methyl-3-phenylindan is passed per hour through the catalyst. The tube wall temperature is 408° C. and the temperature in the interior of the bed of catalyst is 464° C. The gaseous reaction mixture leaving the reactor is cooled to 50° C. so that end product and unreacted 1-methyl-3-phenylindan are condensed. The uncondensed portion is washed out with water. After the wash water has been evaporated, the remaining residue is combined with the condensate.

The following results are obtained:
Starting material: 1-methyl-3-phenylindan—21.56 parts
amount of offgas—500,000 parts by volume
CO and $CO_2$ content in offgas—2.25% by volume
crude end product—18.88 parts.

The following are determined in the end product by ultraviolet absorption:
65% by weight of anthraquinone—12.35 parts
24.2% of phthalic anhydride by weight—4.57 parts
0.1% by weight of unreacted starting material (I)—0.018 part.

This is equivalent to a conversion of 99.9% of the theory and a yield of anthraquinone of 57.2% of theory based on starting material.

EXAMPLE 14

76.0 parts of the catalyst prepared according to Example 9 is placed in a tubular reactor (inside diameter of the tubes 21 mm). A mixture of 100,000 parts by volume of air and 4.03 parts of 1-methyl-3-phenylindan is passed per hour through the catalyst. The tube wall temperature is 416° C. and the temperature in the interior of the catalyst bed is 474° C. The gaseous reaction mixture leaving the reactor is cooled to 50° C. so that the end product and unreacted 1-methyl-3-phenylindan condense. The uncondensed portion is washed with water and the wash water is evaporated off. The remaining residue is united with the condensate.

The following results are obtained:
Starting material: 1-methyl-3-phenylindan—20.13 parts
amount of offgas—500,000 parts by volume
CO and $CO_2$ content in offgas—1.80% by volume
crude end product—17.89 parts.

The following are determined in the crude end product by ultraviolet absorption:
67% by weight of anthraquinone—11.99 parts
19% by weight of phthalic anhydride—3.40 parts
0.06% by weight of unreacted starting material (I)—0.011 part.

This is equivalent to a conversion of 99.9% of theory and a yield of anthraquinone of 59.5% based on reacted starting material.

EXAMPLE 15

83.0 parts of the catalyst prepared according to Example 10 is placed in a tubular reactor (inside diameter of the tubes 21 mm). A mixture of 100,000 parts by volume of air and 3.99 parts of 1-methyl-3-phenylindan is passed per hour through the catalyst. The tube wall temperature is 417° C. and the temperature in the interior of the bed of catalyst is 452° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is combined with the condensate.

The following results are obtained:
Starting material: 1-methyl-3-phenylindan—19.95 parts
amount of offgas—500,000 parts by volume
CO and $CO_2$ content in offgas—1.9% by volume
crude end product—17.83 parts.

The following are determined in the crude end product by ultraviolet absorption:
57% by weight of anthraquinone—10.17 parts
18% by weight of phthalic anhydride—3.21 parts
0.48% by weight of unreacted starting material—0.086 part.

This is equivalent to a conversion of 99.6% of theory and a yield of anthraquinone of 50.9% of theory, based on reacted starting material.

EXAMPLE 16

78.0 parts of catalyst prepared according to Example 11 is placed in a tubular reactor (inside diameter of the tubes 21 mm). A mixture of 100,000 parts by volume of air and 3.68 parts of 1-methyl-3-phenylindan is passed per hour through the catalyst. The tube wall temperature is 426° C. and the temperature in the interior of the bed of catalyst is 450° C. The gaseous reaction mixture leaving the reactor is cooled to 50° C. so that the end product and the unreacted 1-methyl-3-phenylindan are condensed. The uncondensed portion is washed with water. After the wash water has been evaporated, the remaining residue is united with the condensate.

The following results are obtained:
Starting material: 1-methyl-3-phenylindan—18.40 parts
amount of offgas—500,000 parts by volume CO and CO$_2$ content in offgas—1.48% by volume
crude end product—15.69 parts.
The following are determined in the crude end product by ultraviolet absorption:
  60.8% by weight of anthraquinone—9.54 parts
  18% by weight of phthalic anhydride—2.82 parts
  0.40% by weight of unreacted starting material (I)—0.063 part.
This is equivalent to a conversion of 99.7% of theory and a yield of anthraquinone of 51.8% of theory.

Production of a vanadium-boron catalyst

EXAMPLE 17

A mixture of 17.57 parts of vanadium pentoxide and 0.93 part of boron oxide (particle size less than 200 microns) is sprayed onto 152.1 parts of steatite spheres having a diameter of 3 mm by means of flame spraying equipment. The catalyst is then sintered at about 650° C.

Oxidation

EXAMPLE 18

78.0 parts of the catalyst prepared according to Example 17 is placed in a tubular reactor (inside diameter of the tubes 21 mm). A mixture of 100,000 parts of air and 3.68 parts of 1-methyl-3-phenylindan is passed per hour through the catalyst. The tube wall temperature is 430° C. and the temperature in the interior of the catalyst bed is 470° C. The gaseous reaction mixture leaving the reactor is cooled to 50° C. so that the end product and the unreacted 1-methyl-3-phenylindan are condensed. The uncondensed portion is washed with water. After the wash water has been evaporated, the remaining residue is combined with the condensate.
The following results are obtained:
  Starting material: 1-methyl-3-phenylindan—18.40 parts
  amount of offgas—500,000 parts by volume
  CO and CO$_2$ content in offgas—1.80% by volume
  crude end product—15.94 parts.
The following are determined in the crude end product by ultraviolet absorption:
  65.7% by weight of anthraquinone—10.40 parts
  23% by weight of phthalic anhydride—3.67 parts
  less than 0.03% by weight of unreacted starting material (I)—less than 0.005 part.
This is equivalent to a practically quantitative conversion and a yield of anthraquinone of 56.9% of the theory based on reacted starting material.

Production of vanadium-thallium catalysts

EXAMPLE 19

A mixture of 13.60 parts of vanadium pentoxide and 1.10 parts of thallium nitrate (TlNO$_3$—having a particle size of less than 200 microns) is sprayed onto 152.1 parts of steatite spheres having a diameter of 3 mm by means of flame spraying equipment. The catalyst is then sintered at about 650° C.

EXAMPLE 20

The catalyst is prepared analogously to Example 19, a mixture of 13.13 parts of vanadium pentoxide and 0.066 parts of thallium nitrate being sprayed onto 152.1 parts of steatite spheres.

EXAMPLE 21

The catalyst is prepared analogously to Example 19, a mixture of 15.84 parts of vanadium pentoxide and 0.16 part of thallium nitrate being sprayed onto 152.1 parts of steatite spheres.

EXAMPLE 22

The catalyst is prepared analogously to Example 19, a mixture of 14.96 parts of vanadium pentoxide and 3.74 parts of thallium nitrate being sprayed onto 152.1 parts of steatite spheres.

Oxidation

EXAMPLE 23

79.0 parts of the catalyst prepared according to Example 19 is placed in a tubular reactor (inside diameter of the tubes 21 mm). A mixture of 100,000 parts by volume of air and 3.73 parts of 1-methyl-3-phenylindan is passed per hour through the catalyst. The tube wall temperature is 410° C. and the temperature in the interior of the bed of catalyst is 460° C. The gaseous reaction mixture leaving the reactor is cooled to 50° C. so that the end product and the unreacted 1-methyl-3-phenylindan are condensed. The uncondensed portion is washed with water. After the wash water has been evaporated, the remaining residue is united with the condensate.
The following results are obtained:
  Starting material: 1-methyl-3-phenylindan—18.66 parts
  amount of offgas—500,000 parts by volume
  CO and CO$_2$ content in offgas—1.31% by volume
  crude end product—17.56 parts.
The following are determined in the crude end product by ultraviolet absorption:
  68.7% by weight of anthraquinone—12.07 parts
  13% by weight of phthalic anhydride—2.28 parts
  less than 0.03% by weight of unreacted starting material (I)—less than 0.005 part.
This is equivalent to an almost quantitative conversion and a yield of anthraquinone of 64.6% of theory based on reacted starting material.

EXAMPLE 24

82.0 parts of the catalyst prepared according to Example 20 is placed in a tubular reactor (inside diameter of the tubes 21 mm). A mixture of 100,000 parts by volume of air and 3.89 parts of 1-methyl-3-phenylindan is passed per hour through the catalyst. The tube wall temperature is 407° C. and the temperature in the interior of the bed of catalyst is 454° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is combined with the condensate.
The following results are obtained:
  Starting material: 1-methyl-3-phenylindan—19.43 parts
  amount of offgas—500,000 parts by volume
  CO and CO$_2$ content in offgas—2.0% by volume
  crude end product—17.45 parts.
The following are determined in the crude end product by ultraviolet absorption:
  66.0% by weight of anthraquinone—11.52 parts
  18% by weight of phthalic anhydride—3.14 parts
  less than 0.03% by weight of unreacted starting material (I)—less than 0.005 part.

This is equivalent to an almost quantitative conversion and a yield of anthraquinone of 59.2% of theory based on starting material reacted.

EXAMPLE 25

78.0 parts of the catalyst prepared according to Example 21 is placed in a tubular reactor (inside diameter of the tubes 21 mm). A mixture of 100,000 parts by volume of air and 3.85 parts of 1-methyl-3-phenylindan is passed per hour through the catalyst. The tube wall temperature is 406° C. and the temperature in the interior of the bed of catalyst is 462° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is united with the condensate.

The following results are obtained:
Starting material: 1-methyl-3-phenylindan—19.23 parts
amount of offgas—500,000 parts by volume
CO and $CO_2$ content in offgas—1.5% by volume
crude end product—16.68 parts.

The following are determined in the crude end product by ultraviolet absorption:

|  | % by weight | parts |
|---|---|---|
| anthraquinone | 71.9 | 11.99 |
| phthalic anhydride | 15.6 | 2.60 |
| unreacted starting material (I) | less than 0.03 | less than 0.005. |

This is equivalent to an almost quantitative conversion and a yield of anthraquinone of 62.4% of theory based on starting material reacted.

EXAMPLE 26

89.0 parts of the catalyst prepared according to Example 22 is placed in a tubular reactor (inside diameter of the tubes 21 mm). A mixture of 100,000 parts by volume of air and 3.69 parts of 1-methyl-3-phenylindan is passed per hour through the catalyst. The tube wall temperature is 408° C. and the temperature in the interior of the bed of catalyst is 455° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is united with the condensate.

The following results ae obtained:
Starting material: 1-methyl-3-phenylindan—18.45 parts
amount of offgas—500,000 parts by volume
CO and $CO_2$ content in offgas—1.33% by volume
crude end product—16.68 parts.

The following are determined in the crude end product by ultraviolet absorption:

|  | % by weight | parts |
|---|---|---|
| anthraquinone | 67.0 | 11.18 |
| phthalic anhydride | 13 | 2.17 |
| unreacted starting material (I) | less than 0.03 | less than 0.005. |

This is equivalent to an almost quantitative conversion and a yield of anthraquinone of 60.6% of theory based on starting material reacted.

EXAMPLE 27

A mixture of 99,000 parts by volume of air and 4.06 parts of 3-phenyl-1,3-dimethylindan is passed per hour over 48 parts of the catalyst prepared according to Example 2 in a manner analogous to Example 4. The tube wall temperature is 385° C. and the temperature in the interior of the bed of catalyst is 438° C. After the reaction mixture leaving the reactor has been worked up analogously to Example 4, the following results are obtained:
Starting material: 3-phenyl-1,3-dimethylindan—12.18 parts
amount of offgas—297,000 parts by volume
CO and $CO_2$ content of offgas—2.8% by volume
crude end product—8.3 parts
The following are determined in the crude end product by ultraviolet absorption:

| anthraquinone | 56.2% by weight | 4.66 parts |
|---|---|---|
| phthalic anhydride | 23% by weight | 1.91 parts. |

This is equivalent to an anthraquinone yield of 38.3% of theory based on reacted starting material.

Production of vanadium-antimony catalysts

EXAMPLE 28

100 parts of powdered vanadium pentoxide is homogeneously mixed with a solution of 7.85 parts of antimony trichloride in 0.5 part of concentrated hydrochloric acid, made neutral with concentrated ammonia solution and evaporated to dryness. Evaporation with fuming is carried out with concentrated nitric acid in order to expel the ammonia as ammonium nitrate, after which the material is fused and powdered. 10.0 parts of the powdered material is applied by means of flame spraying equipment onto 90 parts of silicon carbide spheres having a diameter of from 4 to 6 mm.

Oxidation

EXAMPLE 29

48 parts of the catalyst prepared according to Example 28 is placed in a tubular reactor (inside diameter of the tubes 21 mm). A mixture of 147,000 parts by volume of air and 5.6 parts of 1-methyl-3-phenylindene is passed per hour through the catalyst. The tube wall temperature is 375° C. and the temperature in the interior of the bed of catalyst is 424° C. The gaseous reaction mixture leaving the reactor is cooled to 50° C. so that the end product and the unreacted 1-methyl-3-phenylindene are condensed. The uncondensed portion is washed with water. After the wash water has been evaporated, the residue which remains is united with the condensate.
The following results are obtained:
Starting material: 1-methyl-3-phenylindene—9.8 parts
amount of offgas—264,000 parts by volume
CO and $CO_2$ content in offgas—2.2% by volume
crude end product—7.8 parts.
The following are determined in the crude end product by ultraviolet absorption:

| anthraquinone | 69% by weight | 5.38 parts |
| phthalic anhydride | 20% by weight | 1.56 parts. |

This is equivalent to an anthraquinone yield of 55% of theory based on starting material reacted.

EXAMPLE 30

48 parts of the catalyst prepared according to Example 28 is placed in a tubular reactor (inside diameter of the tubes 21 mm). A mixture of 109,000 parts by volume of air and 5.1 parts of 1-oxo-3-phenylindan is passed per hour through the catalyst. The tube wall temperature is 418° C. and the temperature in the interior of the bed of catalyst is 445° C. The gaseous reaction mixture leaving the reactor is cooled to 50° C. so that the end product and the unreacted 1-oxo-3-phenylindan are condensed. The uncondensed portion is washed with water. After the wash water has been evaporated, the remaining residue is combined with the condensate.

The following results are obtained:
Starting material: 1-oxo-3-phenylindan—10.2 parts
amount of offgas—218,000 parts by volume
$CO_2$ content in offgas—2.8% by volume
crude end product—8.1 parts.
The following are determined in the crude end product by ultraviolet absorption:
50.4% by weight of anthraquinone—4.08 parts
25% by weight of phthalic anhydride—2.02 parts.
This is equivalent to a yield of anthraquinone of 40% of theory based on starting material used.

EXAMPLE 31

48 parts of the catalyst prepared according to Example 28 is placed in a tubular reactor (tube diameter 21 mm). A mixture of 148,000 parts by volume of air and 5.5 parts of 1-phenylnaphthalene is passed per hour through the catalyst. The tube wall temperature is 400° C. and the temperature in the interior of the bed of catalyst is 450° C. The gaseous reaction mixture leaving the reactor is cooled to 50° C. so that the end product and the unreacted 1-phenylnaphthalene is condensed. The uncondensed portion is washed with water. The wash water is evaporated and the remaining residue is combined with the condensate.

The following results are obtained:
Starting material: 1-phenylnaphthalene—11 parts
amount of offgas—296,000 parts by volume
CO and $CO_2$ content—3.8% by volume
crude end product—7.0 parts.
The following are determined in the crude end product by ultraviolet absorption:
40% by weight of anthraquinone—2.8 parts
31% by weight of phthalic anhydride—2.17 parts.
This is equivalent to a yield of anthraquinone of 25% of theory based on reacted starting material.

Production of vanadium-caesium catalysts

EXAMPLE 32

A mixture of 15.37 parts of vanadium pentoxide and 0.031 part of caesium nitrate (particle size less than 200 microns) is sprayed onto 91.7 parts of silicon carbide spheres having a diameter of 4 to 6 mm by means of flame spraying equipment.

EXAMPLE 33

The catalyst is prepared analogously to Example 32, a mixture of 17.51 parts of vanadium pentoxide and 0.088 parts of caesium nitrate being sprayed onto 91.7 parts of silicon carbide spheres.

EXAMPLE 34

The catalyst is prepared analogously to Example 32, a mixture of 18.04 parts of vanadium pentoxide and 0.46 parts of caesium nitrate being sprayed onto 91.7 parts of silicon carbide spheres.

EXAMPLE 35

The catalyst prepared analogously to Example 34 is calcined for fifteen hours at 500° C.

EXAMPLE 36

The catalyst prepared analogously to Example 34 is calcined for fifteen hours at 600° C.

EXAMPLE 37

The catalyst is prepared analogously to Example 32, a mixture of 17.67 parts of vanadium pentoxide and 0.93 part of caesium nitrate being sprayed onto 91.7 parts of silicon carbide spheres.

EXAMPLE 38

The catalyst is prepared analogously to Example 32, a mixture of 16.93 parts of vanadium pentoxide and 1.37 parts of caesium nitrate being sprayed onto 91.7 parts of silicon carbide spheres.

EXAMPLE 39

The catalyst is prepared analogously to Example 32, a mixture of 17.54 parts of vanadium pentoxide and 1.96 parts of caesium nitrate being sprayed onto 91.7 parts of silicon carbide spheres.

EXAMPLE 40

The catalyst is prepared analogously to Example 32, a mixture of 17.60 parts of vanadium pentoxide and 4.40 parts of caesium nitrate being sprayed onto 91.7 parts of silicon carbide spheres.

Oxidation

EXAMPLE 41

44.1 parts of the catalyst prepared according to Example 32 is placed in a tubular reactor (tube diameter 21 mm). A mixture of 100,000 parts by volume of air and 3.90 parts of 1-methyl-3-phenylindan per hour is passed through the catalyst. The tube wall temperature is 420° C. and the temperature in the interior of the bed of catalyst is 442° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is combined with the condensate.

The following results are obtained:
Starting material: 1-methyl-3-phenylindan—19.49 parts
amount of offgas—500,000 parts by volume
CO and $CO_2$ content in offgas—1.92% by volume
crude end product—17.75 parts.
The following are determined in the crude end product by ultraviolet absorption:

| anthraquinone | 61.5% by weight | 10.91 parts |
| phthalic anhydride | 21% by weight | 3.73 parts |
| unreacted starting | | |

| material (I) | 3.1% by weight | 0.55 part. |

This is equivalent to a conversion of 97.2% of theory and a yield of anthraquinone of 57.6% of theory based on reacted starting material.

EXAMPLE 42

48.4 parts of the catalyst prepared according to Example 33 is placed in a tubular reactor (tube diameter 21 mm). A mixture of 100,000 parts by volume of air and 3.80 parts of 1-methyl-3-phenylindan per hour is passed through the catalyst. The tube wall temperature is 425° C. and the temperature in the interior of the bed of catalyst is 451° C. The gaseous reaction mixture leaving the reactor is cooled to 50° C. so that the end product and the unreacted 1-methyl-3-phenylindan are condensed. The wash water is evaporated and the residue which remains is combined with the condensate.

The following results are obtained:
Starting material: 1-methyl-3-phenylindan—18.98 parts
amount of offgas—500,000 parts by volume
CO and $CO_2$ content in offgas—1.60% by volume
crude end product—17.05 parts.

The following are determined in the crude end product by ultraviolet absorption:

| anthraquinone | 63.9% by weight | 10.90 parts |
| phthalic anhydride | 16.2% by weight | 2.76 parts |
| unreacted starting material (I) | 0.16% by weight | 0.027 part. |

This is equivalent to a conversion of 99.9% of theory and a yield of anthraquinone of 57.4% of theory based on reacted starting material.

EXAMPLE 43

48.1 parts of the catalyst obtained according to Example 34 is placed in a tubular reactor (tube diameter 21 mm). A mixture of 100,000 parts of air and 3.74 parts of 1-methyl-3-phenylindan is passed per hour through the catalyst. The tube wall temperature is 435° C. and the temperature in the interior of the bed of catalyst is 452° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is added to the condensate.

The following results are obtained:
Starting material: 1-methyl-3-phenylindan—18.68 parts
amount of offgas—500,000 parts by volume
CO and $CO_2$ content in offgas—1.60% by volume
crude end product—16.40 parts.

The following are determined in the crude end product by ultraviolet absorption:

| anthraquinone | 60.6% by weight | 9.94 parts |
| phthalic anhydride | 7.6% by weight | 1.25 parts |
| unreacted starting material (I) | 8.4% by weight | 1.38 parts. |

This is equivalent to a conversion of 92.6% of theory and a yield of anthraquinone of 57.4% of theory based on reacted starting material.

EXAMPLE 44

45.85 parts of the catalyst prepared according to Example 35 is placed in a tubular reactor (tube diameter 21 mm). A mixture of 100,000 parts by volume of air and 3.86 parts of 1-methyl-3-phenylindan per hour is passed through the catalyst. The tube wall temperature is 445° C. and the temperature in the interior of the bed of catalyst is 466° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue remaining is combined with the condensate.

The following results are obtained:
Starting material: 1-methyl-3-phenylindan—19.29 parts
amount of offgas—500,000 parts by volume
CO and $CO_2$ content in offgas—1.45% by volume
crude end product—18.25 parts.

The following are determined in the crude end product by ultraviolet absorption:
65.1% by weight of anthraquinone—11.88 parts
12% by weight of phthalic anhydride—2.19 parts
2.5% by weight of starting material (I)—0.46 part.

This is equivalent to a conversion of 97.6% of theory and a yield of anthraquinone of 63.1% of theory based on reacted starting material.

EXAMPLE 45

45.85 parts of the catalyst prepared according to Example 36 is placed in a tubular reactor (tube diameter 21 mm). A mixture of 100,000 parts by volume of air and 3.88 parts of 1-methyl-3-phenylindan is passed per hour through the reactor. The tube wall temperature is 440° C. and the temperature in the interior of the bed of catalyst is 462° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is added to the condensate.

The following results are obtained:
Starting material: 1-methyl-3-phenylindan—19.39 parts
amount of offgas—500,000 parts by volume
CO and $CO_2$ content in offgas—1.65% by volume
crude end product—18.65 parts The following are determined in the crude end product by ultraviolet absorption:
67.6% by weight of anthraquinone—12.61 parts
10% by weight of phthalic anhydride—1.87 parts
0.15% by weight of unreacted starting material (I)—0.03 part.

This is equivalent to a conversion of 99.9% of theory and a yield of anthraquinone of 65.1% of theory based on starting material reacted.

EXAMPLE 46

47.3 parts of the catalyst prepared according to Example 37 is placed in a tubular reactor (tube diameter 21 mm). A mixture of 100,000 parts by volume of air and 3.82 parts of 1-methyl-3-phenylindan is passed per hour through the reactor. The tube wall temperature is 437° C. and the temperature in the interior of the bed of catalyst is 452° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is added to the condensate.

The following results are obtained:
Starting material: 1-methyl-3-phenylindan—19.08 parts
amount of offgas—500,000 parts by volume
CO and $CO_2$ content in offgas—1.65% by volume
crude end product—17.70 parts.

The following are determined in the crude end product by ultraviolet absorption:
65.5% by weight of anthraquinone—11.60 parts
17% by weight of phthalic anhydride—3.01 parts
0.27% by weight of unreacted starting material (I)—0.046 part.

This is equivalent to a conversion of 99.8% of theory and a yield of anthraquinone of 61.0% of theory based on starting material reacted.

EXAMPLE 47

46.1 parts of the catalyst prepared according to Example 38 is placed in a tubular reactor (tube diameter 21 mm). A mixture of 100,000 parts by volume of air and 3.92 parts of 1-methyl-3-phenylindan is passed per hour through the reactor. The tube wall temperature is 435° C. and the temperature in the interior of the bed of catalyst is 458° C. The gaseous reaction mixture leaving the reactor is cooled to 50° C. so that the end product and the unreacted 1-methyl-3-phenylindan are condensed. The uncondensed portion is washed with water. After the wash water has been evaporated, the remaining residue is united with the condensate.

The following results are obtained:
Starting material: 1-methyl-3-phenylindan—19.59 parts
amount of offgas—500,000 parts by volume
CO and $CO_2$ content in offgas—1.15% by volume
crude end product—18.45 parts.

The following are determined in the crude end product by ultraviolet absorption.
65% by weight of anthraquinone—11.99 parts
14% by weight of phthalic anhydride—2.58 parts
0.76% by weight of unreacted starting material (I)—0.14 part.

This is equivalent to a conversion of 99.3% of theory and a yield of anthraquinone of 61.7% of theory based on reacted starting material.

EXAMPLE 48

43.9 parts of the catalyst prepared according to Example 39 is placed in a tubular reactor (tube diameter 21 mm). A mixture of 100,000 parts of air and 3.88 parts of 1-methyl-3-phenylindan is passed per hour through the catalyst. The tube wall temperature is 430° C. and the temperature in the interior of the catalyst is 455° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is united with the condensate.

The following results are obtained:
Starting material: 1-methyl-3-phenylindan—19.39 parts
amount of offgas—500,000 parts by volume
CO and $CO_2$ content in offgas—1.55% by volume
crude end product—17.20 parts.

The following are determined in the crude end product by ultraviolet absorption.
66.7% by weight of anthraquinone—11.47 parts
13% by weight of phthalic anhydride—2.24 parts
0.15% by weight of unreacted starting material (I)—0.026 part.

This is equivalent to a conversion of 99.9% of theory and a yield of anthraquinone of 59.3% of theory.

EXAMPLE 49

46.1 parts of the catalyst prepared according to Example 40 is placed in a tubular reactor (tube diameter 21 mm). A mixture of 100,000 parts by volume of air and 3.70 parts of 1-methyl-3-phenylindan is passed per hour through the catalyst. The tube wall temperature is 430° C. and the temperature in the interior of the bed of catalyst is 450° C. The gaseous reaction mixture leaving the reactor is cooled to 50° C. so that the end product and the unreacted 1-methyl-3-phenylindan are condensed. The uncondensed portion is washed with water. After the wash water has been evaporated, the residue which remains is combined with the condensate.

The following results are obtained:
Starting material: 1-methyl-3-phenylindan—18.48 parts
amount of offgas—500,000 parts by volume
CO and $CO_2$ content in offgas—1.65% by volume
crude end product—15.40 parts.

The following are determined in the crude end product by ultraviolet absorption:
60.4% by weight of anthraquinone—9.30 parts
8.8% by weight of phthalic anhydride—1.35 parts
6.8% by weight of unreacted starting material (I)—1.05 parts.

This is equivalent to a conversion of 94.3% of theory and a yield of anthraquinone of 53.3% of theory based on reacted starting material.

We claim:
1. A process for the production of anthraquinone which comprises oxidizing with oxygen in the gas phase, in the presence of a catalyst, an indan having the formula:

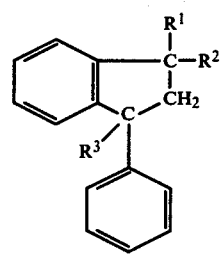

where $R^1$, $R^2$ and $R^3$ may be identical or different and each denotes an alkyl radical, $R^1$ and/or $R^3$ may also each denote hydrogen wherein the reaction is carried out with an indan having the formula (I) in the presence of a catalyst consisting essentially of a vanadium (V) compound and a compound of an element selected from the group consisting of potassium, boron, thallium, antimony and/or caesium, or a diphenylmethane derivative having the formula:

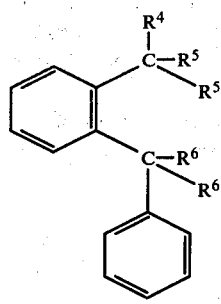 (II), where the individual radicals $R^4$, $R^5$ and $R^6$ may be identical or different and each denotes hydrogen or an alkyl radical having one to eight carbon atoms, or a benzophenone derivative having the formula

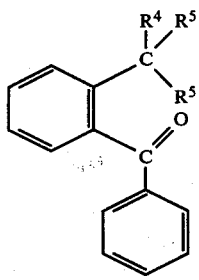 (III), where $R^4$ and $R^5$ have the meanings given above, or an indene having the formula

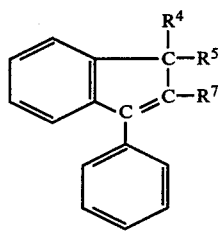 (VI), or

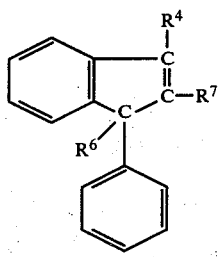 (VII), or an naphthalene derivative having the formula

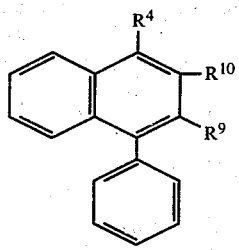 (VIII), wherein $R^4$, $R^5$, $R^6$ and $R^7$ have the meanings given above, $R^9$ and $R^{10}$ may be identical or different and each denotes hydrogen, or one of the two denotes hydrogen and the other an alkyl radical having one to six carbon atoms, or $R^9$ and $R^{10}$ each denotes an alkyl radical and the two radicals having together two to six carbon atoms, as starting material in the presence of a catalyst consisting essentially of a vanadium (V) compound with or without additionally a compound of an element selected from the group consisting of potassium, boron, thallium, antimony and/or caesium, wherein in the process in which an indan (I) is used as the starting material the atomic ratio of vanadium in the catalyst to the additional element or elements is from 1000 to 5 of vanadium to 1 of additional element of potassium, boron, thallium, and antimony, and 2000 to 5 of vanadium to 1 of additional element caesium and wherein the atomic ratio is from 500 to 4 of vanadium to 1 of antimony, from 200 to 15 of vanadium to 1 of potassium, from 500 to 20 of vanadium to 1 of thallium and 20 to 5 of vanadium to 1 of boron and from 1000 to 12 of vanadium to 1 of caesium, wherein said additional element or elements are added to the catalysts in an amount sufficient to obtain at least about 50.9% of theory of an anthraquinone based upon the starting material recited.

2. A process as claimed in claim 1 wherein one of the starting materials II to VIII is employed and wherein the reaction is carried out in the presence of a catalyst of vanadium (V) compound and a compound of potassium, boron, thallium, antimony and/or caesium wherein the atomic ratio of vanadium in the catalyst to the additional element or elements is from 1000 to 5 of vanadium to 1 of additional element of potassium, boron, thallium, and antimony, and 2000 to 5 of vanadium to 1 of additional element caesium and wherein the atomic ratio is from 500 to 4 of vanadium to 1 of antimony, from 200 to 15 of vanadium to 1 of potassium, from 500 to 20 of vanadium to 1 of thallium and 20 to 5 of vanadium to 1 of boron and from 1000 to 12 of vanadium to 1 of caesium.

3. A process as claimed in claim 1 wherein the reaction is carried out using a diphenylmethane derivative (II) as starting material.

4. A process as claimed in claim 1 carried out at a temperature of from 250° to 500° C.

5. A process as claimed in claim 1 wherein the reaction is carried out with a catalyst containing vanadium pentoxide which has been prepared on spheroidal carriers by a flame spraying or plasma spraying method.

6. A process as claimed in claim 1 carried out with from 20 to 2000 grams of starting material (I) or (II) per liter of catalyst (or catalyst on carrier) per hour.

7. A process as claimed in claim 1 carried out with an atomic ratio of 800 to 3 of vanadium to 1 of antimony, 500 to 10 of vanadium to 1 of potassium, less than 800 of vanadium to 1 of thallium, 100 to 1 of vanadium to 1 of boron or 2000 to 5 of vanadium to 1 of caesium.

8. A process as claimed in claim 1 carried out with a catalyst applied to a carrier by a flame spraying or plasma spraying method and then heated to a temperature of from 450° to 650° C. and kept at this temperature for some time.

* * * * *